United States Patent [19]

Gotoh et al.

[11] Patent Number: 5,653,864
[45] Date of Patent: Aug. 5, 1997

[54] PROTEIN BIOSENSOR AND METHOD FOR PROTEIN MEASUREMENT WITH THE SAME

[75] Inventors: Masao Gotoh, Sagamihara; Hiroyuki Nikamoto, Chigasaki; Hiroki Mure, Fujisawa; Shinichi Uchida, Nihonmatsu, all of Japan

[73] Assignee: NOK Corporation, Tokyo, Japan

[21] Appl. No.: 483,414

[22] Filed: Jun. 7, 1995

[30] Foreign Application Priority Data

Jun. 30, 1994 [JP] Japan .................... 6-171703
Nov. 11, 1994 [JP] Japan .................... 6-301671

[51] Int. Cl.⁶ .................................................. G01N 27/26
[52] U.S. Cl. ................................. 205/792; 204/403
[58] Field of Search ........................... 204/403, 290 R, 204/412; 205/792

[56] References Cited

U.S. PATENT DOCUMENTS 4,781,798  11/1988  Gough .................... 205/783
4,871,440  10/1989  Nagata et al. ............ 204/403

FOREIGN PATENT DOCUMENTS

90/12314  4/1990  WIPO .

OTHER PUBLICATIONS

Hitchman et al.; J. Chem. Soc., Faraday Trans. 1; "Potentiometric Monitoring of Proteins"; 1986, 82, 1223-1236 1986 No month available.

Hitchman et al.; Analytica Chimica Acta; "Direct Potentiometric Monitoring of Proteins", 155 (1983) 219-224 1983 No month available.

Yuan et al.; Anal. Chem.; "Determination of Proteins and Denaturation Studies by Flow Injection with a Nickel Oxide Electrode", 1985, 57, 180-185 1985 No month available.

Kelly et al.; J. Chem. Soc., Faraday Trans. 1., "Solid-State Ion Sensors:Theoretical and Practical Issues", 1986, 82, 1195-1208 1986 No month available.

Alexander et al.; Analytica Chimica Acta; "Potentiometric Flow-Injection Determination of Copper-Complexing Organic Ligands with a Copper-Wire Indicating Electrode", 171(1985) 151-163 No month available 1985.

Hui et al.; Analytica Chimica Acta; "Temperature Effects on Amperometric Detection at Nickel Oxide Electrodes in Flow-Injection Systems", 197(1987) 361-365 No month available 1987.

*Primary Examiner*—Kathryn L. Gorgos
*Assistant Examiner*—Alex Noguerola
*Attorney, Agent, or Firm*—Barnes & Thornburg

[57] ABSTRACT

A protein biosensor, which comprises an insulating substrate, a working electrode, a counter-electrode and a reference electrode, each electrodes provided on the insulating substrate, the working electrode comprising a first lead electrode and a thin protein-sensitive metallic film provided on the first lead electrode and the reference electrode comprising a second lead electrode and a silver/silver chloride electrode provided on the second lead electrode is simple in the structure and can be made smaller in the size, enabling easy manufacturing and operation, where measurement of a protein concentration is carried out with a carrier containing KCl or NaCl as dissolved therein.

5 Claims, 11 Drawing Sheets

PROTEIN BIOSENSOR AND METHOD FOR PROTEIN MEASUREMENT WITH THE SAME

BACKGROUND OF THE INVENTION

1. Field of the Invention

The present invention relates to a protein biosensor and a method for protein measurement with the same, and more particularly to a protein biosensor suitable for measuring a protein concentration in urine and a method for protein measurement with the same.

2. Related Art

Protein sensor so far employed comprises a working electrode and a counter-electrode, both in bulk shapes, and a saturated calomel electrode in a glass cylinder form as a reference electrode and thus its size has been inevitably large. Furthermore, the reference electrode made from glass is very brittle and its manufacturing has required very complicated manipulations. Measurement of a protein concentration in urine by a batch procedure or by FIA procedure (Flow Injection Analysis procedure), using these three kinds of electrodes also has such drawbacks as complicated operational setup and handling.

SUMMARY OF THE INVENTION

An object of the present invention is to provide a protein biosensor of simple structure, small size and easy manufacturing and operational setup.

According to the present invention there is provided a protein biosensor, which comprises an insulating substrate, a working electrode, a counter-electrode and a reference electrode, each electrodes provided on the insulating substrate, the working electrode comprising a first lead electrode and a thin protein-sensitive metallic film provided on the first lead electrode and the reference electrode comprising a second lead electrode and a silver/silver chloride electrode provided on the second lead electrode.

DETAILED DESCRIPTION OF THE INVENTION

Figure 1:
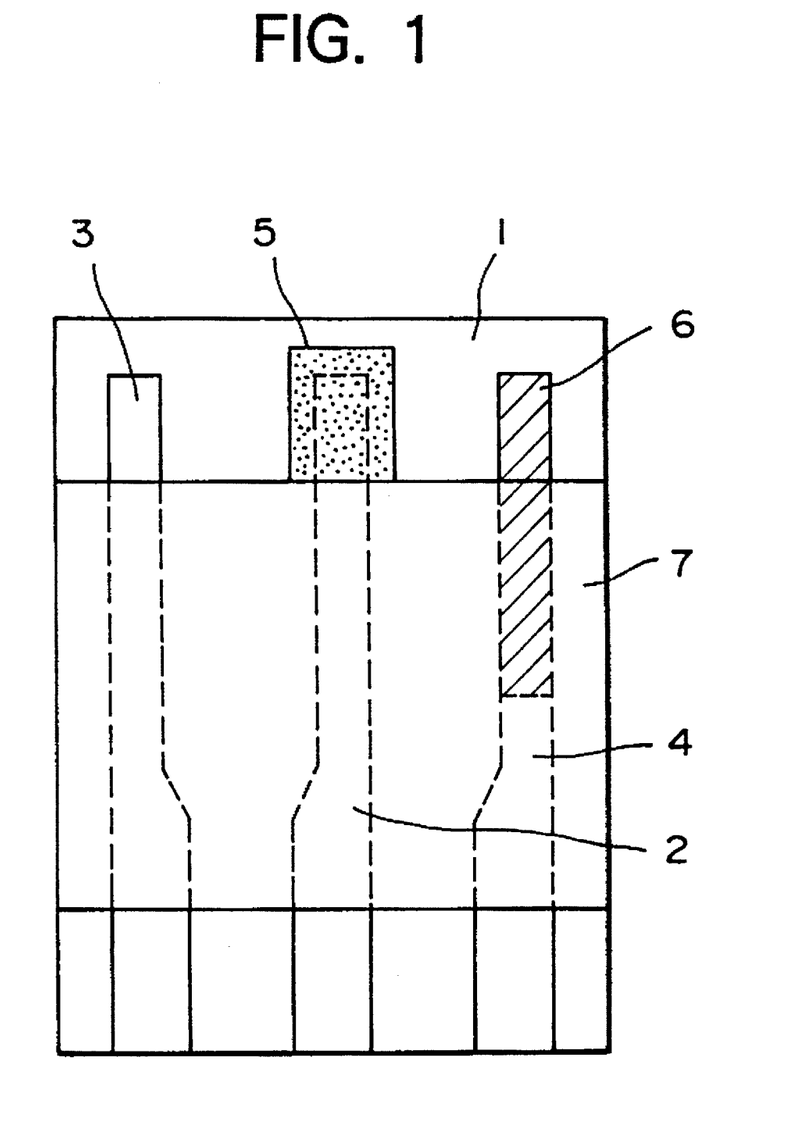
FIG. 1 is a plan view showing a protein biosensor according to one embodiment of the present invention.

FIG. 1 is a plan view showing a protein biosensor according to one embodiment of the present invention, where a first lead electrode 2 for a working electrode, a counter-electrode 3 and a second lead electrode 4 for a reference electrode are each provided on an insulating substrate 1, and a thin protein-sensitive metallic film 5 is provided on a surface part of the first lead electrode 2 to form a working electrode, while a silver/silver chloride electrode 6 is provided on a surface part of the second lead electrode 4 to form a reference electrode.

The term "lead electrode" designates an electrode on a surface part of which a protein-sensitive metallic film is formed to act as a working electrode or a silver/silver chloride electrode is formed to act as a reference electrode.

The present protein biosensor in the above-mentioned structure can be manufactured by forming a first lead electrode 2 for a working electrode, a counter-electrode 3 and a second lead electrode 4 for a reference electrode each on an insulating substrate 1 and then forming a thin protein-sensitive metallic film 5 on a surface part of the first lead electrode 2 and a silver/silver chloride electrode 6 on a surface part of the second lead electrode 4 in any desired order.

As an insulating substrate, plate-shaped, film-shaped or sheet-shaped substrates of glass, ceramics, plastics, etc. can be used in the present invention. A first lead electrode 2 for a working electrode, a counter-electrode 3 and a second lead electrode 4 for a reference electrode are formed on the insulating substrate 1 by an ordinary procedure for forming a thin film from electrode-making materials such as platinum, carbon, silver, gold or the like, respectively.

A thin film 5 of protein-sensitive metal of nickel, copper, silver, cobalt or the like is formed on a surface part of the lead electrode 2 for a working electrode to a film thickness of about 1,000 to about 10,000Å, preferably about 1,000 to about 6,000Å by sputtering, vapor deposition, screen printing, plating or the like.

A silver/silver chloride electrode 6 for a reference electrode is formed on a surface part of the lead electrode 4 for the reference electrode by an ordinary procedure, for example, by forming a silver electrode at first by screen printing, vapor deposition, sputtering, metal plating or the like and then dipping the thus obtained silver electrode on the lead electrode into an aqueous hydrochloric acid solution, followed by constant current electrolysis to convert the silver to silver chloride on the surface part.

Then, the part of the lead electrode 2 for a working electrode other than the part on which the thin protein-sensitive metallic film 5, the part of the counter-electrode 3 other than the tip end part and the part of the lead electrode 4 for a reference electrode other than part or the entirety of the silver/silver chloride electrode 6 are coated with an insulating film 7 of silicone resin, polyimide resin, epoxy resin or the like.

Measurement of a protein concentration, using the present protein biosensor in the above-mentioned structure, is carried out according to the following mechanism.

When the thin protein-sensitive metallic part of the working electrode is made of, for example, nickel, nickel is converted to nickel hydroxide $Ni(OH)_2$ upon contact with a strong alkaline solution, and when a predetermined voltage is applied thereto, nickel hydroxide undergoes the following conversion:

$$Ni(OH)_2 \rightarrow NiO(OH)$$

When the thus formed NiO(OH) is brought into contact with amino groups, thiol groups, hydroxyl groups, etc. as reducible residues of protein, the residues are oxidized, while generating an electric current. By measuring an output of the generated current, a protein concentration can be determined, as shown below:

$$\text{Reducible residues of protein} + NiO(OH) \rightarrow Ni(OH)_2 \rightarrow \text{oxidized protein residues} + ne$$

when n is an integer depending on the oxidation state of protein residues, that is, the number of electrons released by the oxidation.

Measurement of a protein concentration with the present protein biosensor according to the above-mentioned mechanism is carried out by a batch procedure or by a FIA procedure. For the measurement, the sensor is placed into a cell and the cell is mounted on a measurement apparatus to measure current outputs corresponding to protein concentrations in a test sample dissolved in a carrier, for example, a human serum albumin concentration, a globlin concentration, etc. in urine. Measurement temperature is usually in a range of room temperature to about 100° C., preferably room temperature to about 60° C. By elevating the temperature it is possible to increase the current outputs.

The carrier for use in the present invention is an aqueous solution containing about 0.1 to about 10 mM $NiSO_4$ and such an amount of NaOH or KOH as to show an alkalinity, where the degree of alkalinity can be changed, depending on a sensor device temperature.

That is, the thin nickel film as a thin protein-sensitive metallic film provided on the platinum surface as a lead electrode for the working electrode undergoes formation of $NiOOH^-$ species as a surface layer in a carrier solution, for example, in an aqueous 0.1 mM $NiSO_4$ solution as a carrier at a pH of 12 to 13 under room temperature conditions. The $NiOOH^-$ species can pass an oxidation current for the oxidation of protein, but the $NiOOH^-$ species is formed only in the above-mentioned pH range and thus under the room temperature conditions any response capable of quantitative determination of protein cannot be obtained outside the above-mentioned pH range.

It seems that $NiOOH^-$ undergoes the following equilibrium reaction on the nickel electrode:

$$NiO + H_2O \rightleftharpoons NiOOH^- + H^+$$

Equilibrium pH value of the reaction can be lowered by elevating the temperature. More specifically, $NiOOH^-$ as a protein-active species can be formed on the electrode surface at a lower alkaline side pH value by heating the sensor device, and a response capable of quantitative determination of protein can be ensured thereby.

In other words, a response capable of quantitative determination of protein can be gradually extended from pH 13 to lower alkaline side pH values by heating the sensor to a temperature of about 30° to about 350° C., preferably about 50° to about 300° C., for example, to a pH range of 13 to 9 by heating the sensor to a temperature of 300° C.

It is desirable to add about 1 to about 2,000 mM, preferably about 10 to about 500 mM, of an inorganic chloride, preferably potassium chloride or sodium chloride, to the aqueous carrier solution. The added inorganic chloride acts on equilibration of AgCl used on the reference electrode, as given below, to stabilize the potential of the reference electrode and enhance the durability of the reference electrode:

$$AgCl + e^- \rightleftharpoons Ag + Cl^-$$

In the actual measurement, the FIA procedure is more frequently used in the following manner, where current outputs from components other than protein contained in test samples are to be eliminated for the protein measurement.

(1) A separation column is provided between a sample injector and a protein biosensor to measure a current output corresponding to a concentration of protein component eluted from the separation column at first.

Figure 2:
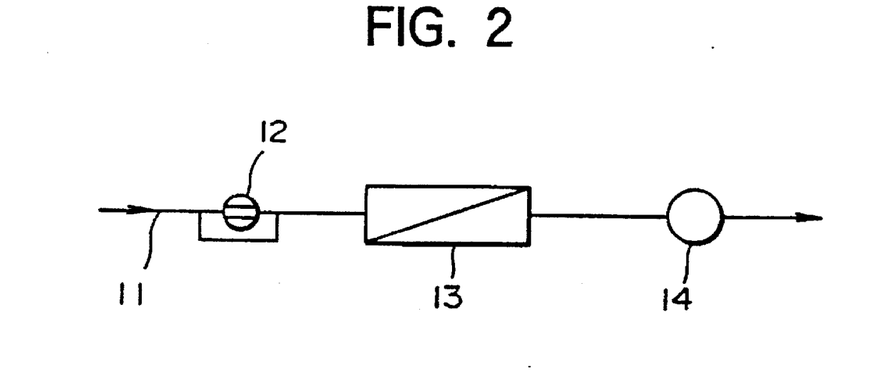
FIG. 2 is a flow diagram showing a first embodiment of the present method for protein measurement.

FIG. 2 is flow diagram of the above-mentioned method for protein measurement based on the FIA procedure. A test sample is injected into a carrier led through a tube 11 by a pump (not shown in the drawing) from a manually-operated or pump-driven sample injector 12 of automatic suction type, and a current output corresponding to a concentration of protein component eluted from a separation column 13 at first is measured by a sensor 14.

Other components contained in a test sample than protein include many kinds of electrode-active compounds such as amino acids, glucose, urea, uric acid, ammonia, creatinine, ascorbic acid, etc., when the test sample is, for example, that of urine, blood, fermentation culture liquor, etc. When the test sample contains these compounds together with protein, selective measurement of protein by the biosensor is difficult to conduct.

To selectively remove these compounds other than the protein, a separation column for selective separation of these compounds is used in the present invention. Fillers for use in the separation column include, for example, fillers for gel chromatography such as dextran gel, acrylamide gel, Hydron gel, Vycol glass, porous silica, styrene gel, etc.; ion-exchangeable fillers such as silica-based ion exchanger, polymeric ion exchange resins, etc.; fillers for adsorptive distribution such as pellicular type, gel type, porous type, etc.; fillers for affinity chromatography such as silica gel or porous polymers having immobilized specific enzyme or antibody; and fillers in a microdomain structure having oleophilic regions and hydrophilic regions distributed with a constant regularity on the surface at the same time, according to the kind of containing materials together.

When, for example, a filler for gel chromatography is used in the separation column and when a test sample containing protein and other compounds together is injected into the separation column, only protein component having a high molecular weight is eluted therefrom at first, while retaining other compounds having lower molecular weights in the separation column by adsorption and thereafter the retained other compounds are eluted therefrom. Thus, the current output of the first eluate, as measured by the biosensor, corresponds to a concentration of protein. This is also true of other cases using other fillers.

Figure 3:
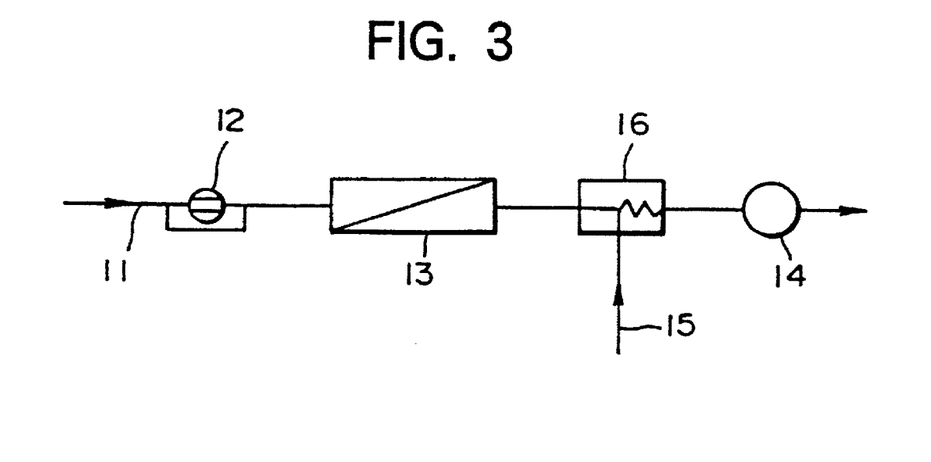
FIG. 3 is a flow diagram showing a modification of the first embodiment.

The current output can be increased with increasing alkalinity, but some of fillers to be packed in the separation column fails to withstand such a higher alkalinity. Or sometimes, it is desired to further increase the pH of a test sample to the biosensor. In that cases, as shown in FIG. 3, another carrier having a higher pH is added to the eluate of protein, for example, at a pH of 5 to 12, at a mixing point 16 through a tube 15 by a pump (not shown in the drawing), and the resulting mixture of elevated pH is led to the sensor 14.

(2) A test sample is passed through a separation membrane having smaller fractionable molecular weights than the molecular weight of protein to measure a current output corresponding to concentrations of components eluted through the separation membrane other than protein and then a current output corresponding to the concentration of protein is obtained by deducting the measured current output from a current output measured for the entire test sample.

Figure 4:
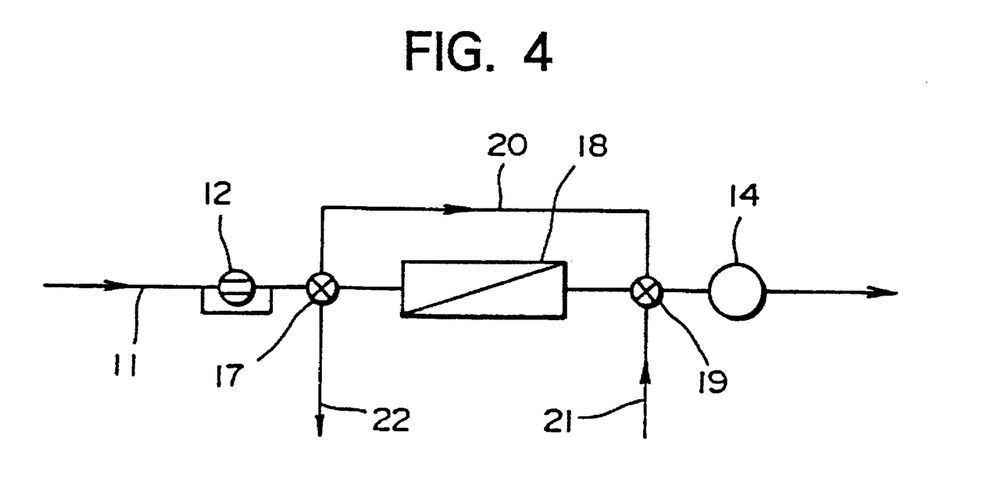
FIG. 4 is a flow diagram showing a second embodiment of the present method.

FIG. 4 is a flow diagram showing the above-mentioned method for protein measurement, where a test sample is injected into a carrier led through a tube 11 by a pump (not shown in the drawing) from a sample injector 12 and passed through a valve 17 and a separation membrane 18, and then to a sensor 14 through another valve 19 to measure a current output corresponding to concentrations of components other than protein. Then, the valves 17 and 19 are so switched that the test sample can bypass the separation membrane 18 and can pass through a tube 20 to the sensor 14. A current output of the bypassed test sample is measured by the sensor 14. A current output corresponding to a concentration of protein contained in the test sample can be obtained by deducting the former output from the latter output.

Separation membranes for use in the present invention includes precision filtration membranes and ultrafiltration membranes in flat film forms, hollow filament forms, tube forms, spiral forms, etc. of porous materials such as polysulfone, cuprammonium cellulose, deacetylated cellulose acetate, acrylonitrile copolymer, polymethyl methacrylate, polyvinyl alcohol, saponified ethylene-vinyl acetate copolymer, aromatic polyamide, carbonate-ethylene oxide copolymer, polyvinylidene fluoride, polyethylene, polypropylene, ceramics, etc. In case of a test sample containing, for example, human serum albumin having a molecular weight of about 70,000, a separation membrane having smaller fractionable molecular weights than about 70,000, for example, fractionable molecular weights of about 50,000, is used, whereby only compounds having molecular weights up to about 50,000 can be passed therethrough without any passage of human serum albumin.

The separation membrane will clog after many runs. When clogged or before clogging occurs, a washing liquor, preferably a washing liquor having the same pH as that of the carrier, is preferably led to the separation membrane 18 through a tube 21 by a pump (not shown in the drawing) and discharged through a tube 22 to conduct a back wash operation.

Figure 5:
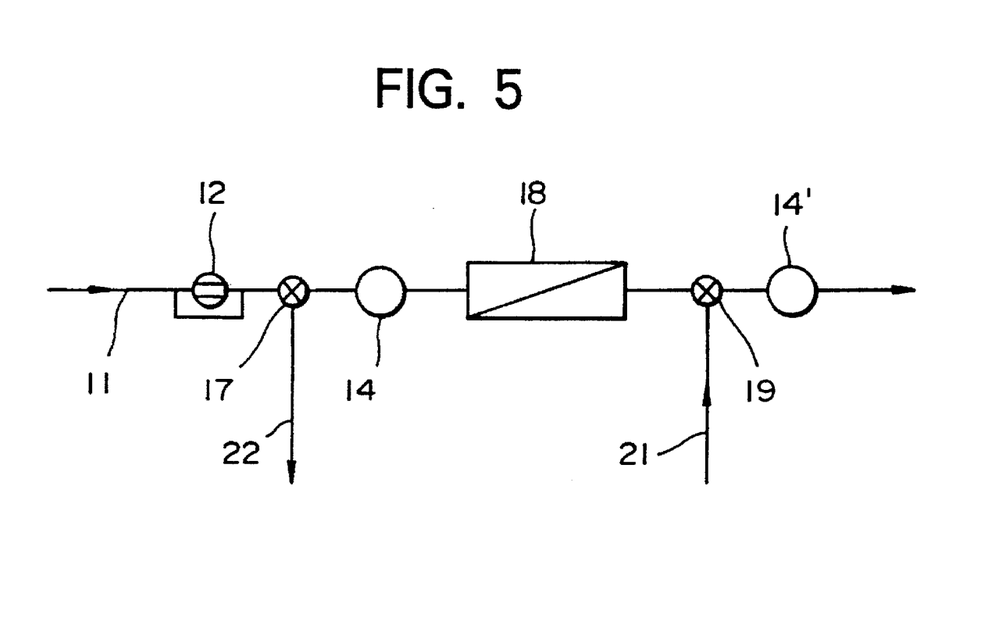
FIG. 5 is a flow diagram showing a modification of the second embodiment.

FIG. 5 is a flow diagram showing another embodiment of the present method for protein measurement based on a current output corresponding to a concentration of protein by deducting a current output corresponding to concentrations of components other than protein from a current output measured for the entire test sample, where a current output of the entire test sample is measured by a sensor 14, and then the test sample is passed through a separation membrane 18. A current output corresponding to components eluted from the separation membrane 18 other than protein is measured by a sensor 14' to determine a difference in the current output as a current output corresponding to a concentration of protein. Back wash operation of the separation membrane 18 is carried out in the same manner as in FIG. 4.

(3) A test sample is passed through a separation membrane having smaller fractionable molecular weights than the molecular weight of protein to elute only components other than protein from the separation membrane, and then the protein retained on the separation membrane is released therefrom by back washing, and a current output is measured for the resulting back wash eluate solution.

Figure 6:
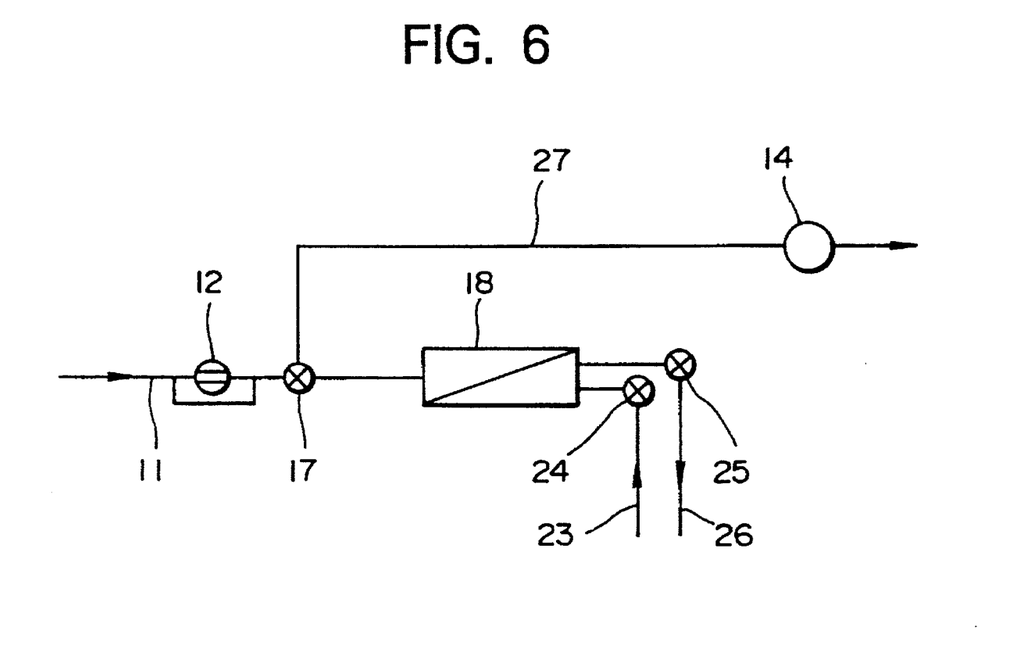
FIG. 6 is a flow diagram showing a third embodiment of the present method.

According to the method for protein measurement shown in the flow diagram of FIG. 6, operations are carried out in the same manner as that for the above-mentioned method (2) until a test sample is passed through a separation membrane having smaller fractionable molecular weights than the molecular weight of protein to elute only components other than protein from the separation membrane, and the eluate is discharged through a valve 25 and a tube 26. Then, the protein retained on the separation membrane is released by back washing, and it is expectable that clogging of the separation membrane can be also effectively prevented thereby at the same time.

That is, back washing is carried out by supplying a carrier having a pH at the same level as or a higher pH to the alkaline side than that of the carrier used for the preparation of the test samples to the separation membrane 18 through a tube 23 and a valve 24, and the resulting back wash eluate is led to the sensor 14 through the valve 17 and a tube 27 to measure a current output corresponding to a concentration of protein.

Furthermore, it has been found in these FIA procedures that a good reproducibility can be obtained by pretreating the thin protein-sensitive metallic film with an aqueous protein solution or an aqueous amino acid solution before the measurement. This finding seems to be based on the following principle.

That is, it seems that NiOOH, an active species for protein or amino acid, is formed, as laid one upon another, on the Ni surface, and above all the outermost NiOOH will change in the quality and quantity with time. Thus, it seems that the calibration level and reproducibility can be improved by reacting such an unstable NiOOH with an aqueous protein solution or an aqueous amino acid solution of a relatively high concentration before starting the measurement, thereby making the NiOOH uniform in the quality and quantity.

The aqueous protein solution for use in the present preteatment includes, for example, aqueous solutions of human serum albumin, bovine serum albumin, etc., and the aqueous amino acid solution for use in the present pretreatment includes, for example, aqueous solutions of glycine, leucine, etc. These aqueous solutions have a high concentration of protein or amino acid, such as about 50 to about 1,000 mg/dl, preferably about 300 to about 700 mg/dl. About 5 to about 500 µl, preferably about 50 to about 200 µl of the aqueous solution, is injected into the cell before measurement of a sample upon pH adjustment of the aqueous solution to about 4 to about 13, preferably about 5 to about 8.

The present biosensor is simple in the structure, because a thin protein-sensitive metallic film is formed only on the lead electrode for a working electrode among the working electrode, a counter-electrode and a reference electrode each electrodes formed on an insulating substrate, and thus the present biosensor can be made smaller in the size and is easy to manufacture and simply operable by either a batch procedure or a FIA procedure and also can make selective detection of protein. Particularly in the FIA procedures, changes in the current output with time, or lowering of the calibration level or reproducibility, can be effectively prevented by pretreating the thin protein-sensitive metallic film with an aqueous protein solution or an aqueous amino acid solution before the measurement.

The silver/silver chloride electrode formed on the lead electrode for a reference electrode can be kept in an AgCl dissociation equilibrium, because a carrier used for the preparation of a test sample contains an inorganic chloride such as potassium chloride, sodium chloride or the like and thus its potential can be stabilized and its durability can be effectively enhanced thereby. Voltage applied at that time is in a range of about 0.01 to about 0.6 V, preferably about 0.1 to about 0.5 V.

Thus the present protein biosensor can make easy measurement of a protein concentration as an indicator for evaluating the function of kidney, particularly a protein concentration in urine and can be widely used in self-caresin the households (in such a mode as a stool-mounted urine protein sensor), urine protein diagnosis in mass medical examination, clinical examination, etc.

PREFERRED EMBODIMENTS OF THE INVENTION

The present invention will be explained in detail below, referring to Examples.

EXAMPLE 1

A platinum counter-electrode, a platinum lead electrode for a working electrode and a platinum electrode for a reference electrode were formed in shapes as shown in FIG. 1 each to a film thickness of 4,000Å on an alumina substrate (A-493, trademark of a product made by kyocera K. K., Japan) by vapor deposition. Then, a silver paste was printed on the lead electrode for the reference electrode by screen printing and baked to form a silver electrode. The thus obtained silver electrode part was dipped into 0.1M hydrochloric acid and subjected to a constant current electrolysis at a current density of 0.6 mA/cm$^2$ for 20 minutes to convert silver to silver chloride on the surface of the lead electrode for the reference electrode. For the constant current electrolysis a potentiogalvanostat (HA-501, trademark of a product made by Hokuto Denko K. K., Japan) was used.

Then, a thin nickel film was formed to a film thickness of 4,000Å at the upper surface of the lead electrode for the working electrode by sputtering with masking the unwanted parts by a metal mask. After the metal mask was removed, silicone resin was provided on the desired surface parts by screen printing to form an insulating film.

The thus prepared sensor was set in a cell and mounted on a FIA measurement apparatus to measure a response to human serum albumin as the main component of urine protein. In the measurement a current detector (LC-4B, trademark of a product made by B. A. S.) was used. Test samples were prepared with an aqueous carrier solution having a pH of 13.0 and containing 0.1 mM NiSO$_4$, 0.1M NaOH and 50 mM KCl. Measurement was conducted under the following conditions:

Distance between sample injector and sensor: 1 m

Sensor cell capacity: 28 μl

Sample injection dose: 100 μl

Used tubes: Teflon tubes, 0.8 mm in inner diameter and 1/16 inch in outer diameter Flow rate: 1.4 ml/min.

Voltage applied to working electrode vs. reference electrode: 0.4 V

Figure 7:
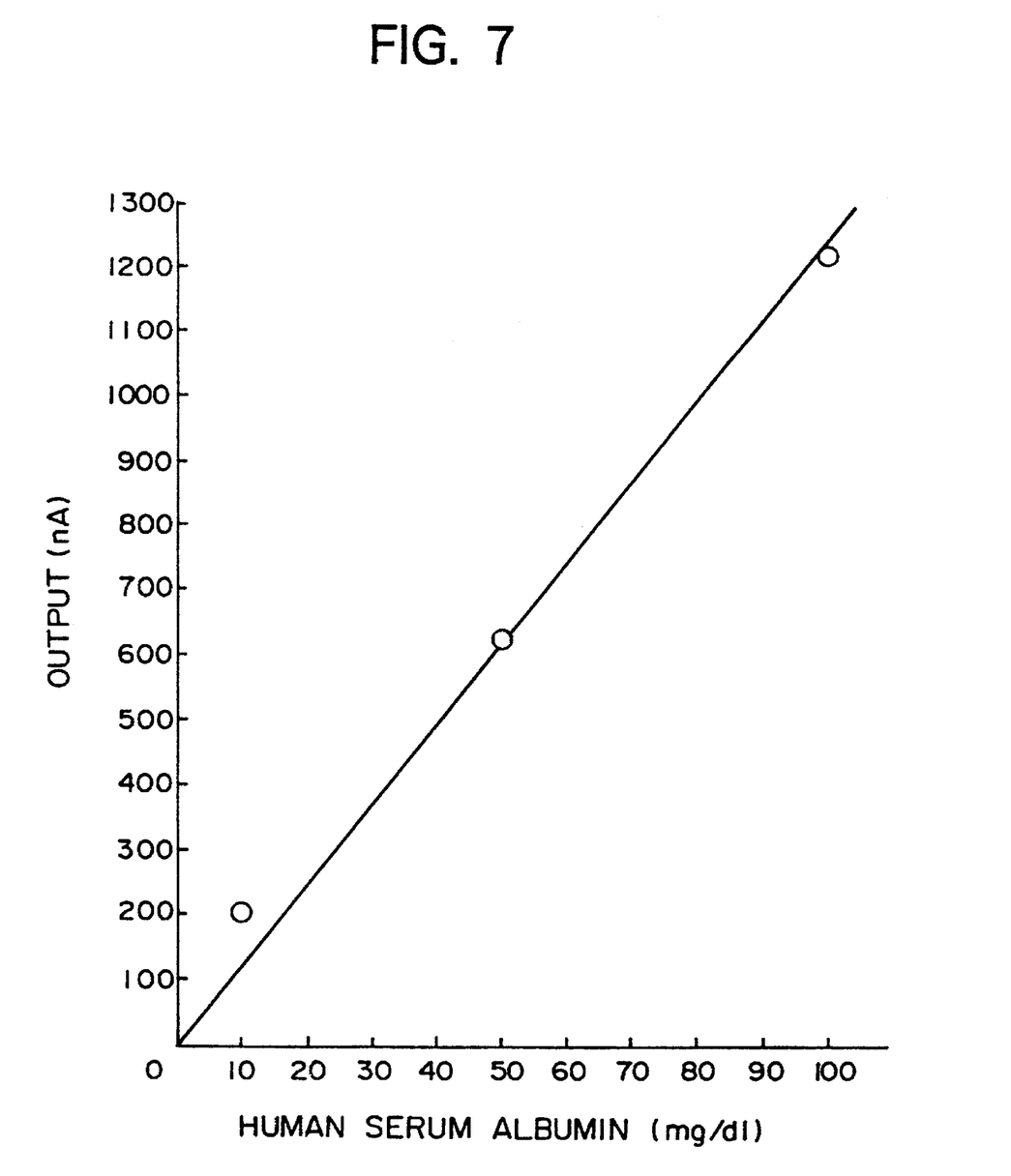
FIG. 7 is a calibration diagram showing measurement results in Example 1.

Output peaks shown in FIG. 7 were obtained for concentrations 10 mg/dl, 50 mg/dl or 100 mg/dl of human serum albumin, and it was found that measurement of protein concentrations could be carried out exactly.

EXAMPLE 2

Measurement of protein concentrations was carried out in the FIA procedure as shown in FIG. 2, using the cell of Example 1 and a current detector (LC-4B). Filler for Gel chromatography was used in the separation column, and test samples were carrier solutions each containing 10 mg/dl, 50 mg dl or 100 mg/dl of human serum albumin and 100 mg/dl of glycin, prepared by an aqueous carrier solution having the same composition as in Example 1, except that the pH was changed to 12.0. Measurement was carried out in the following conditions:

Distance between sample injector and separation column: 1 m

Distance between sample injector and sensor: 1 m

Sensor cell capacity: 28 μl

Sample injection dose: 100 μl

Used tubes: Teflon tubes, 0.8 mm in inner diameter and 1/16 inch in outer diameter Flow rate: 1.4 ml/min.

Voltage applied to working electrode vs. reference electrode: 0.4 V

Figure 8:
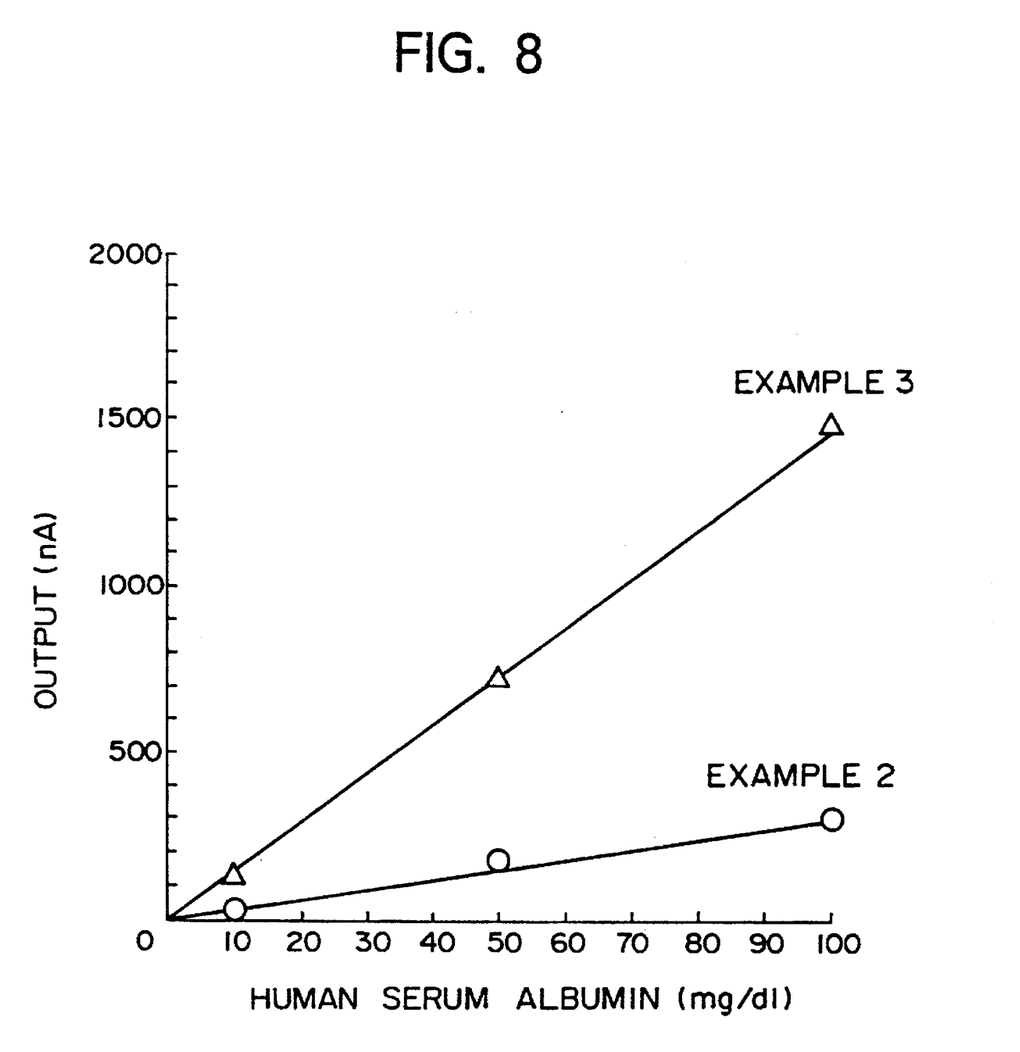
FIG. 8 is a calibration diagram showing measurement results in Examples 2 and 3.

In the measurement of outputs by the sensor, two kinds of peaks were found due to a differnce in the retention time in the separation column, where the eluate obtained at first was that of human serum albumin, .whose output peaks were plotted as shown by a calibration curve in FIG. 8.

EXAMPLE 3

Measurement of protein concentrations was carried out by the FIA procedure as shown in FIG. 3 under the same conditions as in Example 2, except that an aqueous carrier solution of higher alkalinity than that of the first eluate (pH 12.0) from the separation column was added to the first eluate at a mixing point 16 (distance between separation column and mixing point: 50 cm and distance between mixing point and sensor: 50 cm) to make the pH 13.0, and then a current output was measured by the sensor. Output peaks were plotted as shown by a calibration curve in FIG. 8. An increase in the current output was observed.

EXAMPLE 4

Measurement of protein concentrations was carried out by the FIA procedure shown in FIG. 4, using the same cell as prepared in Example 1, a current detector (LC-4B) and a polysulfone hollow filament membrane having fractionable molecular weights of up to 15,000 as a separation membrane. Test samples were carrier solutions each containing 10 mg/dl, 50 mg/dl or 100 mg/dl of human serum albumin and 100 mg/dl of glycin, prepared by an aqueous carrier solution having the same composition and a pH 13 as in Example 1. Conditions for the measurement was the same as in Example 2.

Figure 9:
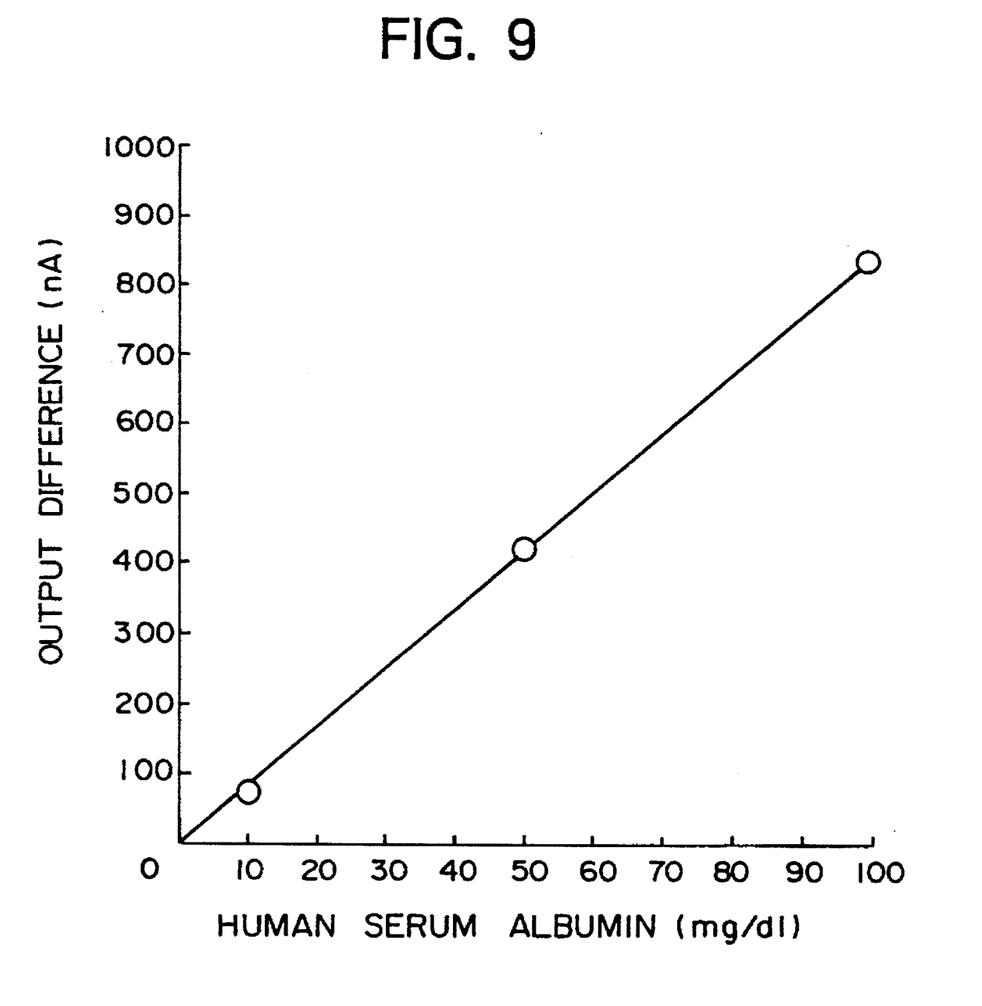
FIG. 9 is a calibration diagram showing measurement results in Example 4.

Measurement was carried out as follows:

At first, a test sample was passed through the separation membrane and a current output (output ①) of eluate (glycin solution) from the separation membrane was measured. Then, a current output (output ②) of the test sample bypassing the separation membrane was measured. Output differences (output ②-output ①) were plotted for human serum albumin (HSA) concentrations, as shown by a calibration curve in FIG. 9.

Plotted output differences were calculated from the following data.

| Test sample | Output ① (nA) | Output ② (nA) | Output difference (nA) |
| --- | --- | --- | --- |
| 10 mg/dl glycin | 485 | 488 | 3 |
| 10 mg/dl glycin + 10 mg/dl HSA | 488 | 563 | 75 |
| 10 mg/dl glycin + 50 mg/dl HSA | 484 | 904 | 420 |
| 10 mg/dl glycin + 100 mg/dl HSA | 486 | 1319 | 833 |

EXAMPLE 5

Figure 10:
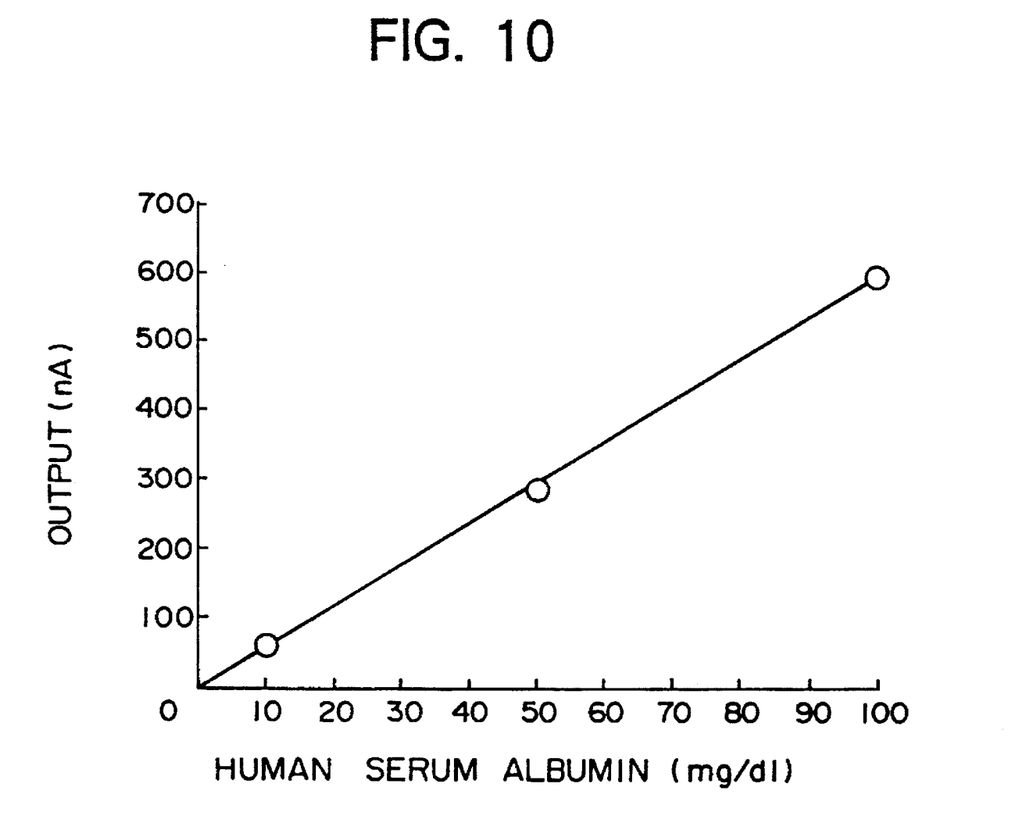
FIG. 10 is a calibration diagram showing measurement results in Example 5.

In Example 4, test samples (except that the aqueous carrier solution had a pH 7.0) was passed through the separation membrane (distance between sample injector and separation membrane: 1 m and distance between separation membrane and sensor: 2 m) to discharge the eluate from the separation membrane. Then, the protein retained on the separation membrane was released therefrom by back washing with a backwash liquor, i.e. an aqueous carrier solution having a pH of 13.0 and a current output of the resulting backwash solution from the separation membrane was measured, as shown calibration curve shown in FIG. 10 was obtained.

EXAMPLE 6

Response to aqueous solutions of human serum albumin as protein using a FIA measurement apparatus on which a cell provided with the sensor prepared in Example 1 was mounted, was determined. Determination was carried out for test samples prepared by an aqueous carrier solution containing 0.1 mM NiSO$_4$ and 50 mM KCl and a pH of 8, 9, 10, 11, 12 or 13 adjusted with NaOH, using a current detector (LC-4B) under the following conditions:

Distance between sample injector and sensor: 1 m

Sensor cell capacity: 30 µl

Sample injection dose: 10 µl

Used tubes: Teflon tubes, 0.8 mm in inner diameter and 1/16 inch in outer diameter Flow rate: 1.4 ml/min.

Voltage applied to working electrode vs. reference electrode: 0.4 V

Sensor device temperature: 25° C., 60° C. or 300° C.

Figure 11:
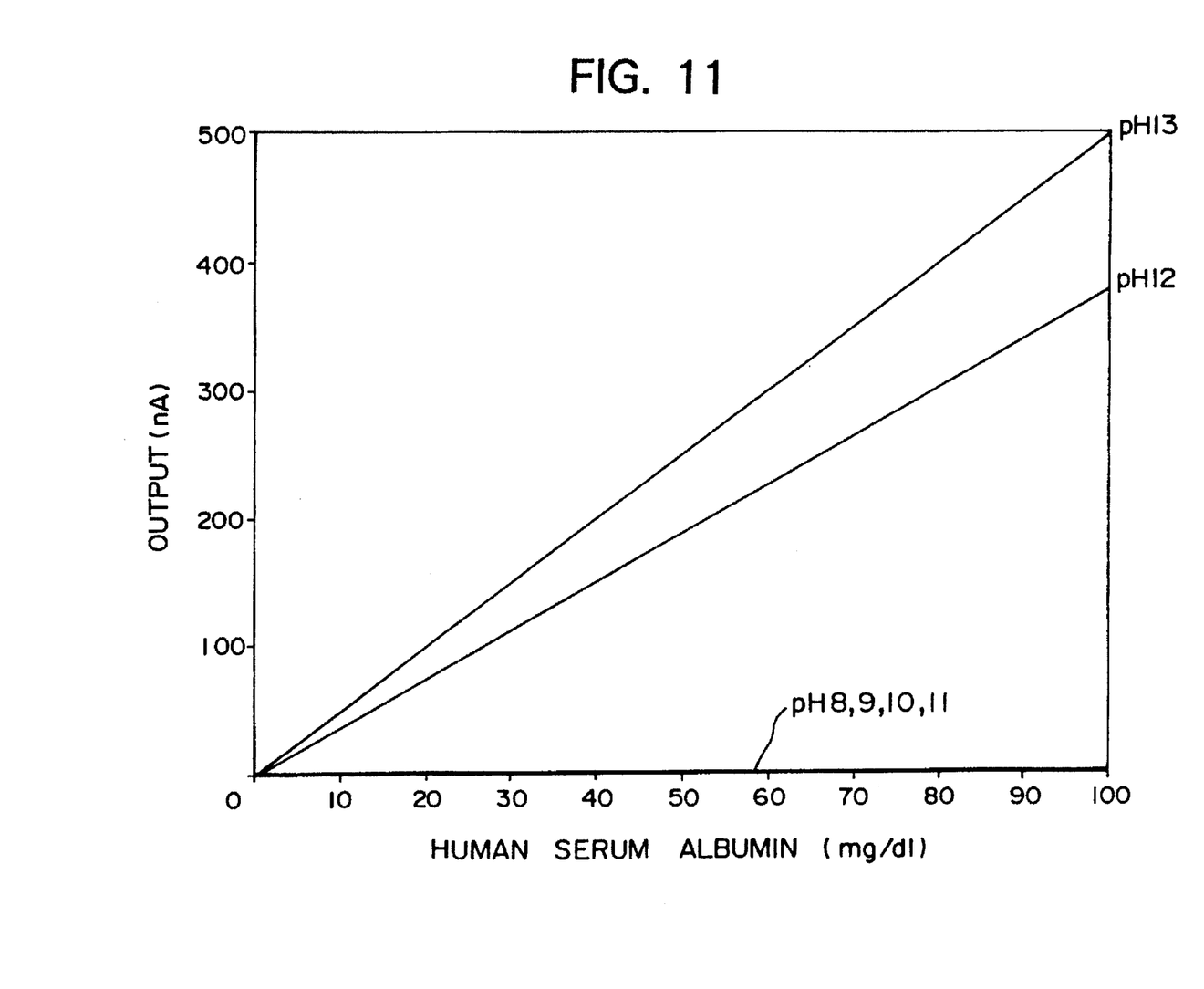
FIG. 11 is a calibration diagram showing measurement results at a sensor device temperature of 25° C. in Example 6.
Figure 12:
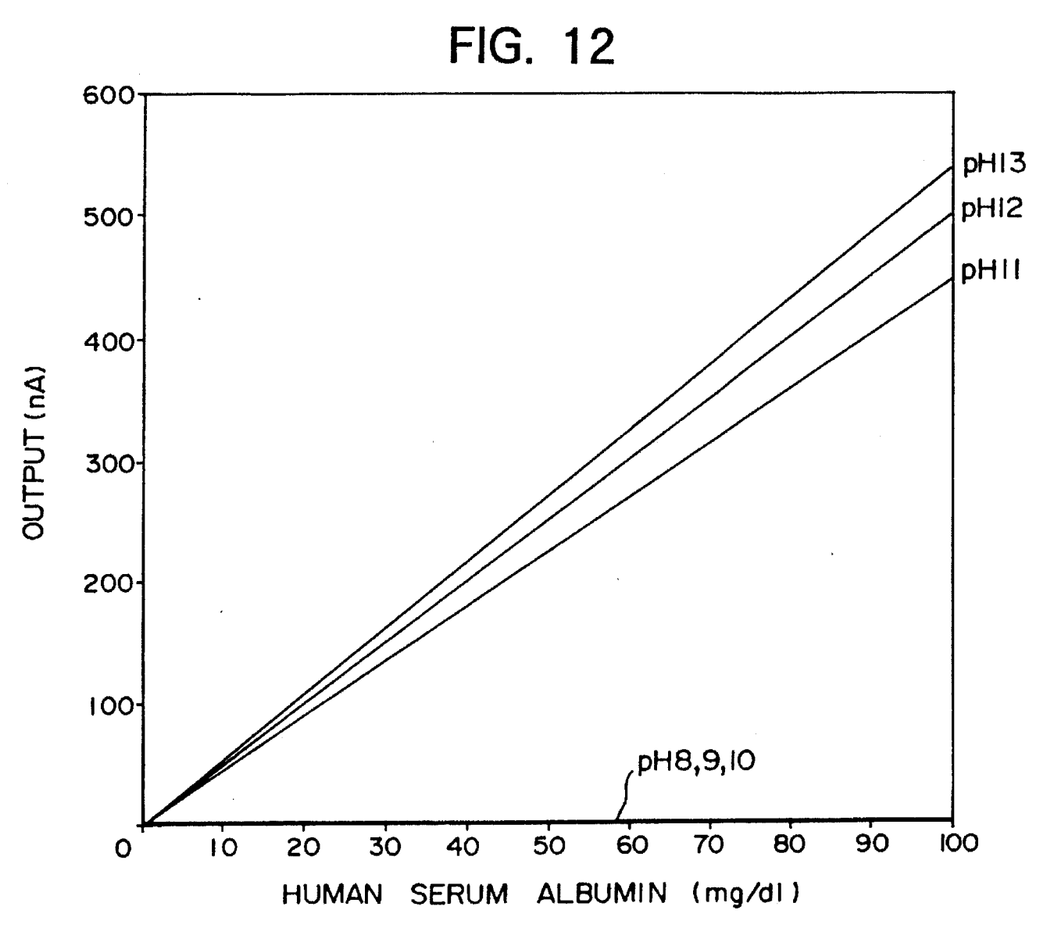
FIG. 12 is a calibration diagram showing measurement results at a sensor device temperature of 60° C. in Example 6.
Figure 13:
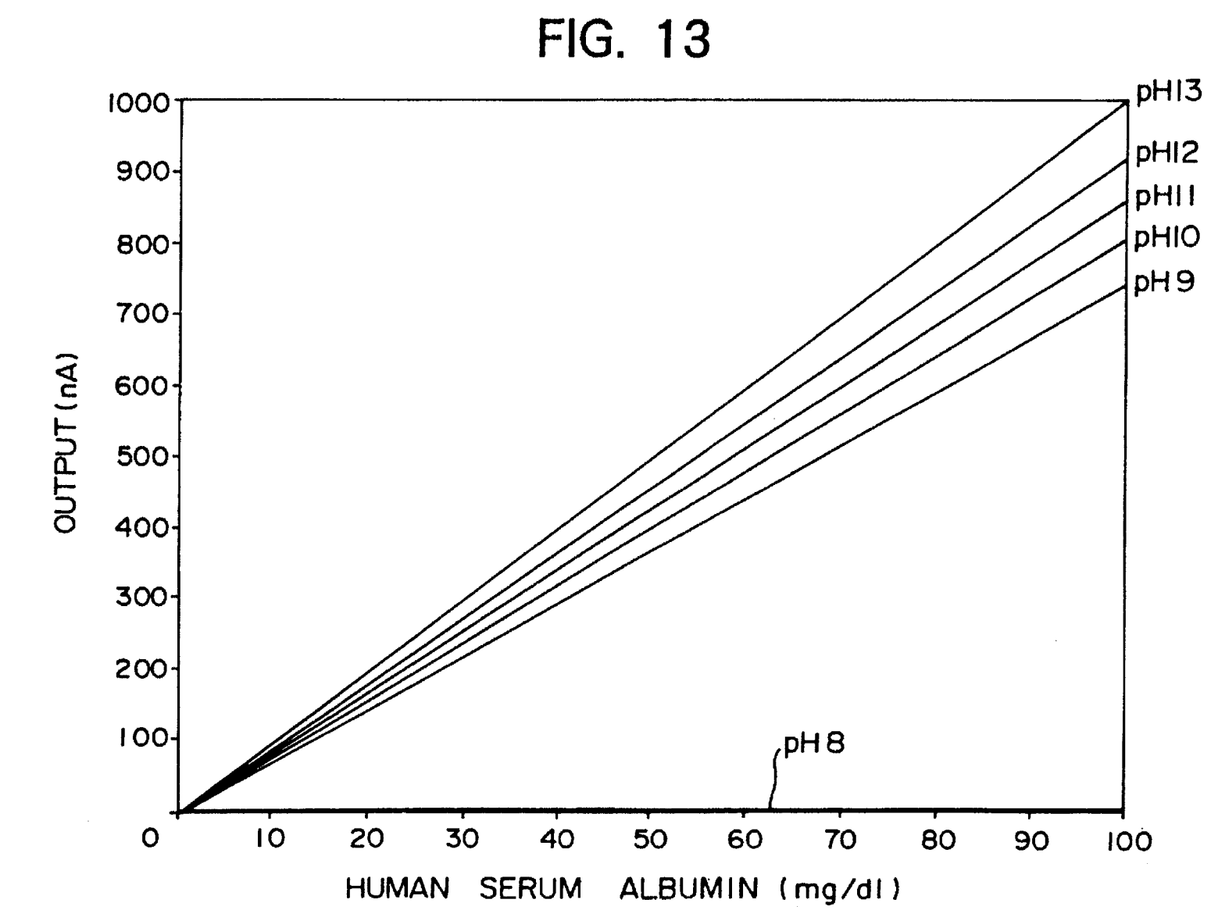
FIG. 13 is a calibration diagram showing measurement results at a sensor device temperature of 300° C. in Example 6.

Calibration curves shown in FIG. 11 (25° C.), FIG. 12 (60° C.) and FIG. 13 (300° C.) were obtained for human serum albumin concentrations 10 mg/dl, 20 mg/dl, 50 mg/dl or 100 mg/dl. As is evident from these results, current outputs proportional to human serum albumin concentrations could be obtained in a pH range of 12 to 13 at the sensor temperature of 25° C., in a pH range of 11 to 13 at 60° C. and in a pH range of 9 to 13 at 300° C. That is, protein concentrations can be exactly measured in such pH ranges.

EXAMPLE 7

The sensor prepared in Example 1 was fixed into a cell and mounted on a FIA measurement apparatus, and 100 µl of an aqueous human serum albumin solution (pH 6.0) having an albumin concentration of 500 mg/dl was injected into the cell to contact the thin protein-sensitive nickel film. The injected human serum albumin solution was removed from the cell by an aqueous carrier solution (0.1 mM NiSO$_4$, 0.1M NaOH, 50 mM KCl; pH 13.0) passing through the tube.

After the above-mentioned pretreatment responses to aqueous human serum albumin solutions having various concentrations, prepared with water (pH 6.0) were measured by a current detecter (LC-4B) under the following conditions:

Distance between sample injector and sensor: 1 m

Sensor cell capacity: 50 µl

Sample injection dose: 100 µl

Used tubes: Teflon tubes, 0.8 mm in inner diameter and 1/16 inch in outer diameter Measurement temperature: 40° C.

Flow rate: 1.4 ml/min.

Voltage applied to working electrode vs. reference electrode: 0.4 V

All-night condition: 0.4 V; power source: on; carrier pump: off

Figure 14:
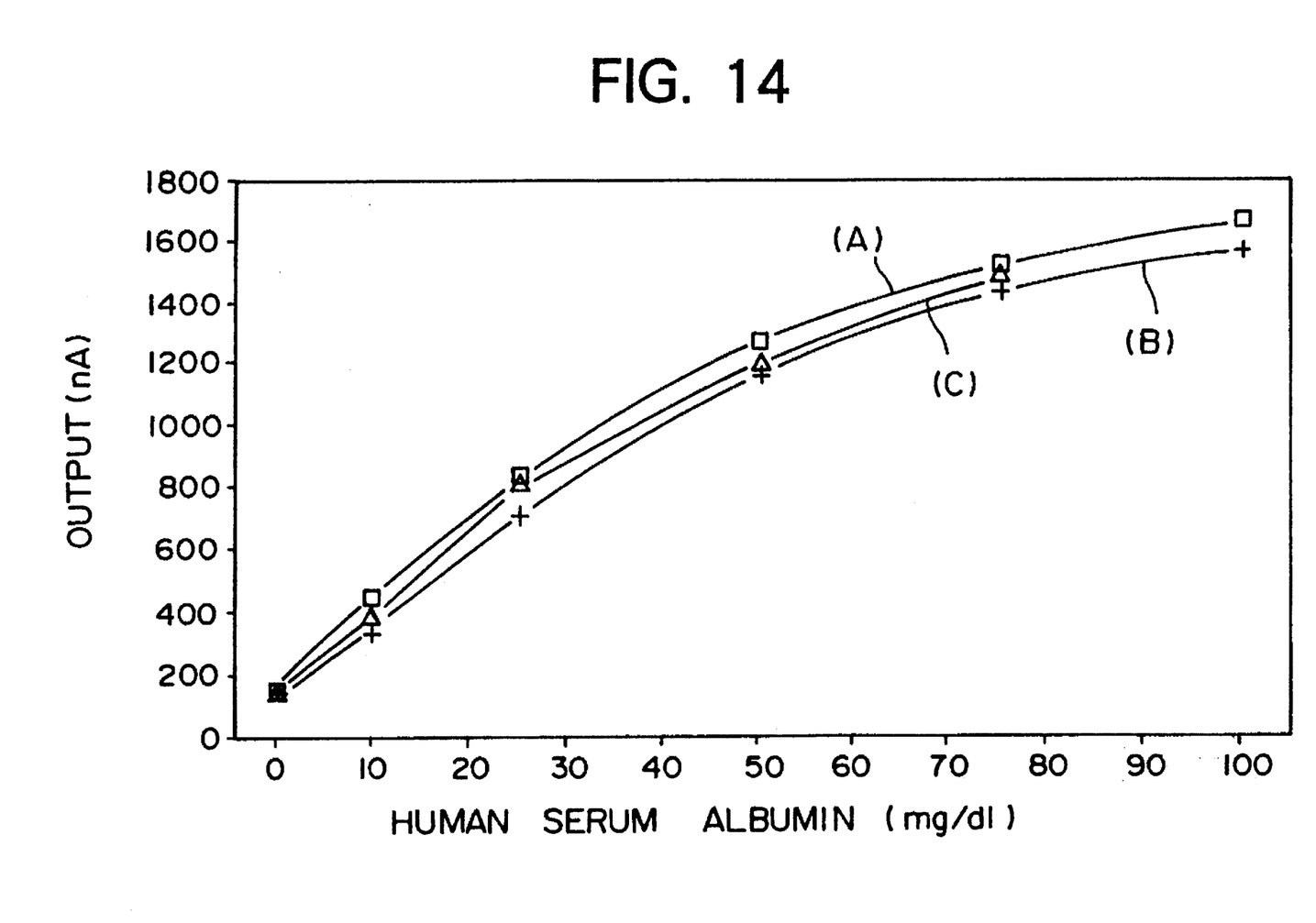
FIG. 14 is a calibration diagram showing measurement results of pretreatment for various human serum albumin concentrations in Example 7.

Calibration level (A) as shown in FIG. 14 was obtained for human serum albumin concentrations of 0, 10, 25, 50, 75 or 100 mg/dl. After 30 days from the initial day of the measurement, pretreatment with an aqueous human serum albumin solution having a concentration of 500 mg/dl was conducted again and the measurement was carried out likewise, whereby calibration level (B) was obtained. After the measurement for calibration level (B), measurement was repeated likewise without any pretreatment with the human serum albumin solution, whereby calibration level (C) was obtained. Calibration levels (B) and (C) had no remarkable changes from calibration level (A) and were found to be good. As to the reproducibility of responses to an aqueous human serum albumin solution having a concentration of 50 mg/dl, a fluctuation factor was 2.0% (n=10) according to the following equation:

$$\text{Fluctuation factor (C. V. value)} = \text{standard deviation/average} \times 100 \; (\%)$$

Without the pretreatment of the thin protein-sensitive metallic film, the fluctuation factor was 6.6% (n=10).

EXAMPLE 8

The sensor prepared in Example 1 was fixed into the cell and mounted onto a FIA measurement apparatus, and the pretreatment with 100 µl of an aqueous glycine solution (pH 6.0) having a concentration of 500 mg/dl and measurements were conducted in the same manner as in Example 7.

Calibration level was determined for human serum albumin concentrations ranging from 0 to 100 mg/dl for the initial day and 30th day. From the resulting results, reproducibility to human serum albumin concentration of 50 mg/dl was determined in the same manner as in Example 7. It was found that fluctuation factor was 2.2% (n=10).

What is claimed is:

1. A method for measuring a protein concentration with a protein biosensor, having an insulating substrate, a working electrode, a counter-electrode and a reference electrode, each electrode provided on the insulating substrate, the working electrode comprising a first lead electrode and a thin nickel film provided on the first lead electrode, and the reference electrode comprising a second lead electrode and a silver/silver chloride electrode provided on the second lead electrode, said method comprising:

treating the protein sensor with an alkaline solution so as to form a NiOOH layer on the nickel electrode surface;

allowing the nickel electrode surface to react with an aqueous protein solution or an aqueous amino acid solution to increase the uniformity of the NiOOH layer before measuring a protein concentration; and contacting the protein sensor with a test sample to measure a protein concentration of the test sample.

2. A method according to claim 1, wherein the test sample is treated with a carrier having inorganic chloride dissolved therein.

3. A method according to claim 2, where the inorganic chloride is potassium chloride.

4. A method according to claim 2, where the inorganic chloride is sodium chloride.

5. A method according to claim 1, wherein the protein biosensor is heated to a temperature of 50° to 350° C. during the measurement.

* * * * *